United States Patent [19]

Atzinger et al.

[11] Patent Number: 5,338,732
[45] Date of Patent: Aug. 16, 1994

[54] MEGESTROL ACETATE FORMULATION

[75] Inventors: Anne E. Atzinger, Lebanon; Robert J. Bequette; Robert E. Davis, both of Evansville, all of Ind.

[73] Assignee: Bristol-Myers Squibb Company, New York, N.Y.

[21] Appl. No.: 882,218

[22] Filed: May 13, 1992

Related U.S. Application Data

[63] Continuation-in-part of Ser. No. 839,061, Feb. 19, 1992, abandoned, which is a continuation of Ser. No. 717,155, Jun. 18, 1991, abandoned.

[51] Int. Cl.$^5$ ............................................. A61K 31/56
[52] U.S. Cl. ............................................... 514/178
[58] Field of Search ....................................... 514/178

[56] References Cited

U.S. PATENT DOCUMENTS

| | | | |
|---|---|---|---|
| 3,356,573 | 12/1967 | Kirk et al. | 167/74 |
| 4,370,321 | 1/1983 | Greaney et al. | 424/243 |
| 4,396,615 | 8/1983 | Petrow et al. | 424/242 |
| 4,402,695 | 9/1983 | Wong | 604/892 |
| 4,666,885 | 5/1987 | Labrie | 514/15 |
| 4,760,053 | 7/1988 | Labrie | 514/15 |
| 4,775,661 | 10/1988 | Labrie | 514/15 |

OTHER PUBLICATIONS

J. H. Von Roenn, et al., Annals of Internal Medicine, 109, 840-841 (1988).

*Primary Examiner*—Marianne M. Cintins
*Assistant Examiner*—Kimberly R. Jordan
*Attorney, Agent, or Firm*—Thomas R. Savitsky; Michelle A. Kaye

[57] ABSTRACT

The present invention relates to a novel oral pharmaceutical composition of micronized megestrol acetate at a concentration of 15 to 150 mg/mL comprising polysorbate at a concentration of 0.005% to 0.015% weight-/volume and polyethylene glycol at a concentration of 5-30% weight/volume which composition forms a stable flocculated suspension in water. The invention further comprises the micronized megestrol acetate formulation described above with added preservatives, buffers, sweeteners and flavoring agents.

10 Claims, No Drawings

MEGESTROL ACETATE FORMULATION

BACKGROUND OF THE INVENTION

This application is a continuation-in-part of 07/839,016, now abandoned, which is a continuation of 07/717,155, filed on Jun. 18, 1991 now abandoned.

This invention relates to a pharmaceutical composition containing megestrol acetate. Megestrol acetate is the generic name for 17-alpha-acyloxy-6-methylpregna-4,6diene-3,20-dione distributed by Bristol-Myers Squibb Corporation under the proprietary name Megace as an anti-neoplastic drug.

Kirk, et al, U.S. Pat. No. 3,356,573 disclose a megestrol acetate pharmaceutical tablet preparation comprising lactose, magnesium stearate and starch. Also, Kirk, et al, commented that liquid compositions of megestrol acetate can take the form of solutions, emulsions, suspension, syrups and elixirs but provide no details as to the composition of such formulations.

Petrow, et al, U.S. Pat. No. 4,396,615 discloses a method of treating androgen-related disorders by administering 6-methyleneprogesterone derivatives concurrently with megestrol acetate but do not elaborate on what constitutes the megestrol acetate formulation.

Greaney, et al, U.S. Pat. No. 4,370,321, disclose adjuvant therapy for the treatment of breast cancer employing megestrol acetate. The type or composition of the megestrol acetate formulation is not specifically described Labrie, U.S. Pat. No. 4,666,885 discloses combination therapy for treatment of female breast cancer comprising the administration of luteinizing hormones in combination with an anti-androgen such as megestrol acetate. In particular, the '855 patent at column 8, lines 58–61, discloses that the anti-androgens are formulated with conventional pharmaceutical excipients (e.g., spray dried lactose and magnesium stearate) into tablets or capsules for oral administration.

Labrie, U.S. Pat. No. 4,760,053 relates to a treatment of sex steroid dependent cancers by combination therapy which includes the use of megestrol acetate but does not describe the type or composition of pharmaceutical formulation used in the treatment.

Labrie, U.S. Pat. No. 4,775,661 relates to combination therapy for treatment of female breast cancer in which megestrol acetate is disclosed as a suitable steroidal anti-androgen. Further, it is disclosed that megestrol acetate, as an active substance, may be mixed with binders such as polyethylene glycol and may include taste improving substances which can be worked into tablets or dragee cores.

J.H. Von Roenn, et al, Annals of Internal Medicine, 109, 840–841 (1988) describe use of megestrol acetate for treatment of cachexia associated with human immunodeficiency virus (HIV) infection. The dose of megestrol acetate was reported but not the type or composition of the formulation.

Currently, megestrol acetate is available for therapeutic purposes in tablet form. The prior art referred to above is notably lacking in descriptions of pharmaceutical compositions of megestrol acetate other than tablets or capsules.

In view of the widespread use of megestrol acetate in clinical medicine, it would be desirable to have a liquid pharmaceutical dosage form in those cases where patients are unable to swallow tablets or capsules or where a high dose would require the ingestion of a relatively large number of tablets.

SUMMARY OF THE INVENTION

It is, therefore, an object of the invention to provide an oral liquid pharmaceutical dosage form of megestrol acetate.

It is another object of the invention to provide an oral liquid pharmaceutical composition of megestrol acetate in the form of a suspension.

It is another object of the invention to provide an oral liquid pharmaceutical composition, of megestrol acetate in the form of a flocculated suspension.

It is yet another object of the invention to provide a pharmaceutical composition of megestrol acetate in the form of a flocculated suspension which does not defloculate during the shelf-life of the product.

It is also another object of the invention to provide an oral liquid dosage form of megestrol acetate in water dispersion which will remain readily dispersible throughout a minimum shelf life of two years, thereby assuring a uniform dose of megestrol acetate.

In accordance with the present-invention, an oral pharmaceutical composition of megestrol acetate is provided comprising micronized megestrol acetate in combination with polysorbate and polyethyleneglycol with buffering, sweetening and flavoring agents added for palatability.

Other objects and advantages of the present invention will become apparent from the following description and appended claims.

DETAILED DESCRIPTION OF THE INVENTION

A preferred embodiment of the invention constitutes an oral pharmaceutical composition comprising micronized megestrol acetate at a concentration of 15 to 150 mg/mL in combination with a polysorbate at a concentration of 0.005% to 0.015% weight/volume (w/v) and a polyethylene glycol at a concentration greater than 5% w/v which composition forms a stable flocculated suspension in water. A preferred embodiment of the invention provides an oral pharmaceutical composition comprising micronized megesterol acetate at a concentration of 15 to 150 mg/mL, preferably at 20 to 120 mg/mL, and most preferably at 40 mg/mL.

A suspension is a particular class of dispersion having an internal (suspended) phase made up of particulate matter which is essentially insoluble in, but dispersed uniformly throughout, an external phase consisting of suspending medium or vehicle. In the most preferred formulation of the invention, the internal phase comprises micronized megestrol acetate having a mass median diameter between 3 and 10 microns; and the external phase is composed essentially of purified water plus polysorbate 80, polyethylene glycol 1450, xanthan gum, sodium benzoate, citric acid, sodium citrate, sucrose and flavors.

A flocculated suspension has a loose aggregation (floccule) of particulate matter wherein discrete particles are held together in a network-like structure. The floccule, referred to as a "stable floc", usually contains varying amounts of entrapped liquid medium or vehicle within the network-like structure and tend to cluster together in weak aggregates. Flocculated suspensions do not cake upon standing and are easily dispersed by shaking. Formulation of a flocculated suspension generally requires adjustment of surfactant, wetting agent, protective colloid/suspending agent in order to provide a stable floc which will resist deflocculation or agglomeration and thereby possible caking. Preservatives, buffers, sweeteners and flavors are also used. Selection of excipients is critical as relatively minor changes can affect the properties of a stable flocculated suspension formulation.

Megestrol acetate, a hydrophobic solid, is not easily wetted by water and has a relatively high interfacial tension accentuated by entrapped air absorbed on the surface of the particle. Hence, the use of a surfactant and wetting agent are required to provide a suspension and maintain physical stability.

The flocculated suspension of megestrol acetate of this invention requires that megestrol acetate be micronized so that 90% of the weight of particles is below 20 microns and the mass median diameter is between 3.0 and 10 microns, and that the micronized particles are dispersed in water with surfactant or wetting agent such as polysorbate 80 and polyethylene glycol 1450 which are present to reduce interfacial tension between the particle, entrapped gas and water. The amount of surfactant or wetting agent are particularly critical in providing a stable floc. According to R.A. Nash, Chap. 5, page 181., Pharmaceutical Suspensions, Pharmaceutical Dosage Forms, Marcel Decker, New York, the usual concentration of a surfactant varies from 0.05 to 0.5% w/v and depends on the solids content intended for suspension. Examples of such suspensions are given in Table 1 which lists some currently marketed steroid suspensions (1989 Physicians Desk Reference, 43rd Edition) and the polysorbate 80 surfactant concentration.

TABLE 1

Percent of Polysorbate 80 Concentration Used in Steroid Suspensions According to Physician's Desk Reference, 43rd Edition

| Steroid | Steroid Conc. mg/ml | Polysorbate 80 percent w/v |
| --- | --- | --- |
| Aristocort Forte | 40 | 0.2 |
| Artistospan | 20 | 0.4 |
|  | 5 | 0.2 |
| Cortone Acetate | 25 to 50 | 0.4 |
| Decadron - LA | 8 | 0.075 |
| Depo-Provera | 100 | 0.184 |
| Hydeltra-T.B.A. | 20 | 0.1 |
| Hydrocortone Acetate | 25 to 50 | 0.4 |
| Kenalog-40 | 40 | 0.04 |

Megestrol acetate suspensions prepared at polysorbate concentrations indicated above are not stable in that deflocculation and caking occurs.

In order to achieve the instant stable flocculated megestrol acetate suspension, the polysorbate concentration must be at about or less than 0.02% w/v, preferably from 0.005% to 0.015% w/v and most preferably 0.01% w/v. At polysorbate 80 concentrations as low as 0.025% w/v there is significant deflocculation and caking. At polysorbate concentrations at or below 0.005–0.01% w/v, a physically stable product was obtained but there is increased difficulty with respect to wetting of the micronized megestrol acetate at these low concentrations. Surfactants having properties similar to polysorbate 80 can also be used. In this regard, polysorbate 85 has acceptable wetting properties. Other surfactants which can be used are polysorbate 20, 40, 60, and 65.

Wetability and suspendability of the micronized megestrol acetate are enhanced by using a hydrophilic polymer. In this regard, the hydrophilic polymer preferred for the megestrol acetate suspension formulation of the invention is polyethylene glycol (PEG) 1450 at a concentration of from 5 to 30% w/v, preferably from 12 to 24% w/v, and most preferably 20% w/v. A 30% w/v PEG 1450 concentration results in some handling problems due to higher suspension viscosity but otherwise provides a suspension with acceptable physical properties. Suspensions made with less than 8% PEG 1450 required additional effort to wet the drug and were found to be undesirable in that there was a small residual percentage of the drug in a dry state which contained entrapped air and then floated on the surface of the liquid. Polyethylene glycol 3350 at a 3% w/v concentration is less effective than PEG 1450 in making a completely wetted suspension. Other grades of PEG can be employed at the preferred concentrations including those having average molecular weights of from about 400 to 4000. PEG 1450 is particularly preferred because higher molecular weights develop high viscosities and low molecular weights detract from taste.

Xanthan gum is preferably used as a suspending agent at about 0.2% w/v. The use of a suspending agent maintains the megestrol acetate particles in a uniformly suspended state for a longer period of time during the dose administration period thereby permitting uniform dosing. Xanthan gum is a high molecular weight polysaccharide having thixotropic properties with immediate viscosity recovery. In this regard, xanthan gum at a concentration of 0.1–0.3% w/v provides the most useful and elegant dosage form and is preferred, with a concentration of 0.2% w/v most preferred.

Conventional preservatives, buffers, sweeteners and flavoring agents are employed. In this regard, the following are preferred:
Preservative-sodium benzoate at 0.2% w/v,
Buffer-citric acid and sodium citrate at 0.244 and 0.015% w/v, respectively.
Sweetener-sucrose at 5% w/v,
Flavor-lemon lime at 0.91% w/v.

EXAMPLE 1

Megestrol Acetate Composition

A lemon-lime flavored oral suspension containing 40 mg of megestrol acetate per milliliter has the following composition.

EXAMPLE 2

Megestrol Acetate Composition

A lemon-lime flavored oral suspension containing 120 mg of megestrol acetate per milliliter has the following composition.

TABLE 2

Megestrol Acetate Composition

| Ingredient | Quantity per ml | % w/v |
| --- | --- | --- |
| Megestrol acetate, micronized | 40 mg | 4 |
| Polyethylene Glycol 1450 | 200 mg | 20 |
| Polysorbate 80 | 0.1 mg | 0.01 |
| Xanthan Gum, TF | 2.0 mg | 0.2 |
| Sodium Benzoate | 2.0 mg | 0.2 |
| Citric Acid | 2.44 mg | 0.244 |
| Sodium Citrate | 0.15 mg | 0.015 |
| Sucrose | 50.0 mg | 5.0 |
| N & A Lemon-Lime Flavor #400639 | 0.91 mg | 0.091 |

TABLE 2-continued

Megestrol Acetate Composition

| Ingredient | Quantity per ml | % w/v |
|---|---|---|
| Purified Water | q.s. 1.0 ml | |

TABLE 3

Megestrol Acetate Composition

| Ingredient | Quantity per ml | % w/v |
|---|---|---|
| Megestrol acetate, micronized | 120 mg | 12 |
| Polyethylene Glycol 1450 | 200 mg | 20 |
| Polysorbate 80 | 0.1 mg | 0.01 |
| Xanthan Gum, TF | 2.0 mg | 0.2 |
| Sodium Benzoate | 2.0 mg | 0.2 |
| Citric Acid | 2.44 mg | 0.244 |
| Sodium Citrate | 0.15 mg | 0.015 |
| Sucrose | 50.0 mg | 5.0 |
| N & A Lemon-Lime Flavor #400639 | 0.91 mg | 0.091 |
| Purified Water | q.s. 1.0 ml | |

Preparation of the megestrol acetate suspension, using proportional amounts of the ingredients, is carried out as follows. Approximately 90% of the PEG is melted (heated) and combined with an equivalent weight of water and the polysorbate 80 to make a solution. The solution is cooled to room temperature and micronized megestrol acetate added and dispersed using a Lightin mixer with a high shear blade such as a Jiffy, Cowles or Hockmeyer blade. Xanthan gum is separately dispersed in approximately 10% of the melted PEG and this gum slurry then added to water to uniformly hydrate the gum. This procedure allows the gum to be rapidly hydrated and uniformly dispersed in water. The citrates, sucrose, sodium benzoate, and flavor are then added to the gum dispersion and the gum slurry passed through a screen. Next, the gum dispersion and the megestrol acetate dispersion are combined and mixed to provide a uniform oral suspension. The entire suspension is then passed through a colloid mill or homogenizer to provide an oral suspension containing 40 mg/ml of megestrol acetate. Suspensions containing from 75 to 200 mg/mL of megestrol acetate were prepared in a similar manner.

EXAMPLE 3

Suspension Stability

One of the major considerations in assessing acceptability of a suspension is the tendency of the suspension to flocculate. Generally, the greater the flocculation, the better the redispersibility. A common method for evaluating this is measurement of the sedimentation height. This is a convenient and practical approach to the determination of the physical stability of the megestrol acetate suspension system. Essentially, the method comprises use of a volumetric graduated cylinder to determine the settling rates of the flocculated suspension by making periodic measurements of sedimentation height without disturbing the system.

Sedimentation height as a percent of the initial total suspension height is given in Table, 4 for varying concentrations of polysorbate 80 in the formulation of Examples 1 and 2.

TABLE 4

| PS 80 Concentration Percent w/v | Sedimentation Height Percent of Initial Height | | |
|---|---|---|---|
| | Time (weeks) | | |
| | 0 | 4 | 15 |
| 0.005 | 100 | 91 | 68 |
| 0.01 | 100 | 90 | 70 |
| 0.02 | 100 | 94 | 25 |
| 0.03 | 100 | 91 | 29 |

It is evident that the relative degree of flocculation of megestrol acetate suspension at PS80 concentrations of 0.005 w/v and 0.01 w/v is substantially better than that found with PS80 concentrations 0.02 w/v or greater.

EXAMPLE 4

Suspension Stability of PEG 1450

Concentrations of PEG 1450 in the formulation of Examples 1 and 2 were varied from 5 to 20% w/v. Sedimentation height at time intervals were determined and are given in Table 5.

TABLE 5

| PEG 1450 Concentration Percent w/v | Sedimentation Height Percent of Initial Height | | |
|---|---|---|---|
| | Time (weeks) | | |
| | 0 | 4 | 15 |
| 20 | 100 | 77 | 52 |
| 15 | 100 | 85 | 57 |
| 10 | 100 | * | 59 |
| 8 | 100 | * | 59 |
| 6 | 100 | * | * |
| 5 | 100 | * | * |

*Poor wetting of particles and entrapped air indicated by settled particles and particles at top with clear liquid between.

It is evident that the lower limit of PEG 1450 is between 10 and 15% w/v in the above variation of the formulation of Examples 1 and 2.

EXAMPLE 5

Suspension Stability of Polysorbate 80

Concentrations of PS80 were varied from 0.005 to 0.025 percent w/v in the formulation of Examples 1 and 2 without the added suspending agent xanthan gum. Sedimentation height at time intervals were determined and are given in Table 6.

TABLE 6

| Polysorbate 80 Percent w/v | Sedimentation Height Percent of Initial Height | | | | |
|---|---|---|---|---|---|
| | 0.005 | 0.01 | 0.015 | 0.02 | 0.025 |
| Day 0 | 100 | 100 | 100 | 100 | 100 |
| Day 1 | 55 | 51 | 44 | 44 | 45 |
| Day 2 | 51 | 48 | 41 | 39 | 16 |
| Day 3 | 49 | 45 | 41 | 39 | 14 |
| Day 6 | 48 | 45 | 41 | 38 | 14 |
| Day 36 | 46 | 44 | 39 | 35 | 13 |
| Supernatant Appearance on Day 36 | Clear | Clear | Hazy | Cloudy | Cloudy |

This example supports the longer term results of Example 3 in that while flocculation is seen at all tested concentrations of PS80, levels of 0.005 to about 0.015 percent w/v provide flocculated suspensions with superior stability.

What is claimed is:

1. An oral pharmaceutical composition comprising micronized megestrol acetate at a concentration of 15 to 150 mg/mL in combination with polysorbate at a concentration of 0.005% to 0.015% weight/volume and polyethylene glycol at a concentration of greater than 5% weight/volume which composition forms a stable flocculated suspension in water.

2. The composition of claim 1 wherein the concentration of micronized megestrol acetate is 20 to 120 mg/mL.

3. The composition of claim 1 wherein the concentration of micronized megestrol acetate is 40 mg/mL.

4. The composition of claim 1 wherein polysorbate 80 is employed.

5. The composition of claim 1 wherein the concentration of polyethylene glycol is from 5% to 30% weight/volume.

6. The composition of claim 1 wherein the concentration of polyethylene glycol is 12 to 24% weight/volume.

7. The composition of claim 1 wherein the concentration of polyethylene glycol is 20% weight/volume.

8. The composition of claim 1 wherein the concentration of polysorbate is 0.01% weight/volume.

9. The composition of claim 1 with buffering, sweetening and flavoring agents.

10. An oral pharmaceutical composition comprising on a percent weight/volume basis megestrol acetate 4%, polyethylene glycol 1450 20%, polysorbate 80 0.01% xanthan gum 0.2%, sodium benzoate 0.2% citric acid 0.244%, sodium citrate 0.015%, sucrose 5%, lemon-lime flavor 0.091%, and the remainder purified water which composition forms a stable flocculated suspension in water.

* * * * *